United States Patent [19]

Bey

[11] Patent Number: 4,551,550
[45] Date of Patent: Nov. 5, 1985

[54] N-2,3-BUTADIENYL-1,4-BUTANEDIAMINE DERIVATIVES

[75] Inventor: Philippe Bey, Cincinnati, Ohio

[73] Assignee: Merrell Dow Pharmaceuticals Inc., Cincinnati, Ohio

[21] Appl. No.: 682,396

[22] Filed: Dec. 17, 1984

[51] Int. Cl.$^4$ .................. C07C 103/127; C07C 87/24
[52] U.S. Cl. ...................................... 564/215; 564/509
[58] Field of Search ............................... 564/215, 509

[56] References Cited

U.S. PATENT DOCUMENTS

| | | | |
|---|---|---|---|
| 2,073,363 | 3/1937 | Carothers et al. | 564/509 X |
| 2,136,177 | 11/1937 | Carothers et al. | 564/509 X |
| 3,692,851 | 9/1972 | Henrick et al. | 564/509 X |
| 4,173,649 | 11/1979 | Sundeen et al. | 564/509 X |
| 4,426,321 | 1/1984 | Ochsner | 564/509 X |

Primary Examiner—Paul F. Shaver
Attorney, Agent, or Firm—Raymond A. McDonald; William J. Stein; Gary D. Street

[57] ABSTRACT

1. A compound of the formula:

$$H_2C=C=CHCH_2NHCH_2-Z-CH_2NHR$$

wherein:
Z is —$CH_2CH_2$— or trans-$CH=CH$—,
R is H, $CH_3$—, $CH_3CH_2$, $CH_3(CH_2)_2$—, —$(CH_2)_3NH_2$, —$(CH_2)_3NHCOCH_3$, —$CH_2CH=CH_2$, or —$CH_2CH=C=CH_2$,
or a pharmaceutically acceptable acid addition salt thereof are inhibitors of polyamine oxidase.

17 Claims, No Drawings

N-2,3-BUTADIENYL-1,4-BUTANEDIAMINE DERIVATIVES

Polyamine oxidase (PAO) is an enzyme which is present in high amounts in most mammalian tissues. PAO is responsible for the degradation of $N^1$-acetylspermidine and $N^1$-acetylspermine, to putrescine and spermidine, respectively [See F. Bolkerius et al., Int. J. Biochem. 13, 287 (1981)]. Hence, PAO is a key enzyme of the catabolic side of the polyamine interconversion pathway [See N. Seiler et al., Medical Biology, 59, 334 (1981)].

The present invention is directed to a novel class of chemical compounds whose structural formulae are represented by Formula I below:

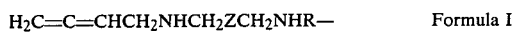   Formula I wherein:
Z is —$CH_2CH_2$— or trans—CH=CH—,
R is H, $CH_3$—, $CH_3CH_2$, $CH_3(CH_2)_2$—, —$(CH_2)_3NH_2$, —$(CH_2)_3NHCOCH_3$, —$CH_2CH=CH_2$, or —$CH_2CH=C=CH_2$, or a pharmaceutically acceptable acid addition salt thereof.

Examples of the compounds of Formula I are:

A. When Z is —$CH_2CH_2$—:
 i R=H:
  N-2,3-butadienyl-1,4-butanediamine
 ii R=$CH_3$—, $CH_3CH_2$—, or $CH_3CH_2CH_2$—:
  $N^1$-2,3-butadienyl-$N^4$-methyl-1,4-butanediamine
  $N^1$-2,3-butadienyl-$N^4$-ethyl-1,4-butanediamine
  $N^1$2,3-butadienyl-$N^4$-propyl-1,4-butanediamine
 iii R=—$CH_2CH=C=CH_2$:
  $N^1$, $N^4$-2,3-butadienyl-1,4-butanediamine
 iv R=—$CH_2CH=CH_2$:
  $N^1$-2,3-butadienyl-$N^4$-1-propenyl-1,4-butanediamine
 v R=—$(CH_2)_3NH_2$;
  $N^1$-2,3-butadienyl-$N^4$-aminopropyl-1,4-butanediamine
 vi R=—$(CH_2)_3NHCOCH_3$:
  $N^1$-2,3-butadienyl-$N^4$-acetylaminopropyl-1,4-butanediamine B. When Z is (trans)—CH=CH—:
 vii R=H:
  (E)-N-2,3-butadienyl-2-butene-1,4-diamine
 viii R=$CH_3$—:
  (E)-N-2,3-butadienyl-$N^4$-methyl-2-butene-1,4-diamine
  (E)-N-2,3-butadienyl-$N^4$-ethyl-2-butene-1,4-diamine
  (E)-N-2,3-butadienyl-$N^4$-propyl-2-butene-1,4-diamine
 ix R=—$CH_2CH=C=CH_2$:
  (E)-$N^1$,$N^4$-2,3-butadienyl-2-butene-1,4-diamine
 x R=—$CH_2CH=CH_2$:
  (E)-$N^1$-2,3-butadienyl-$N^4$-1-propenyl-2-butene-1,4-diamine
 xi R=—$(CH_2)_3NH_2$:
  (E)-$N^1$-2,3-butadienyl-$N^4$-aminopropyl-2-butene-1,4-diamine
 xii R=—$(CH_2)_3NHCOCH_3$:
  (E)-$N^1$-2,3-butadienyl-$N^4$-acetylaminopropyl-2-butene-1,4-diamine Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as organic carboxylic acids, for example salicylic maleic, malonic, tartaric, citric and ascorbic acids and organic sulfonic acids, for example methane sulfonic acid.

The compounds of Formula I are irreversible inhibitors of polyamine oxidase (PAO) as can be demonstrated in vitro and in vivo in biochemical test procedures. The biochemical testing of illustrative compounds for their ability to inhibit PAO is illustrated herein in Examples 7 and 8.

Inhibitors of PAO are of particular interest for the study of the physiological role of the polyamine interconversion pathways in mammals. Additionally, inhibitors of PAO prevent the degradation of $N^1$-acetylspermidine with the concomitant formation of putrescine. The ability to decrease the amount of circulating putrescine in mammals would be highly advantageous with certain conditions, such as for example, in situations of enhanced cell proliferation.

It is believed that the compounds of Formula I are "substrate-induced irreversible inhibitors" of PAO. Such inhibitors are also known in the art as "enzyme-activated irreversible inhibitors", "suicide enzyme inhibitors", "$K_{cat}$ inhibitors", or "mechanism-based inhibitors". In order for a compound to be a substrate-induced irreversible enzyme inhibitor, the compound must be a substrate for the target enzyme, and the compound must contain a latent reactive group susceptible to being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the compounds of Formula I generally exert their action by means of a substrate-induced mechanism, inhibition may occur by other mechanisms, such as by competitive inhibition.

In general, the compounds of Formula I can be prepared by treating a compound Formula II:

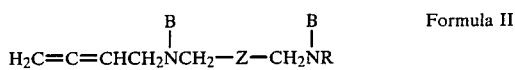   Formula II wherein:
Z is —$CH_2$—$CH_2$— or (trans)-CH=CH—,
B is an amino-protecting group, and
R is —H, —$CH_3$, —$CH_2CH_3$, —$CH_2CH_2CH_3$, —$(CH_2)_3NH_2$, —$(CH_2)_3NHCOCH_3$, —$CH_2CH=CH_2$, or —$CH_2CH=C=CH_2$;
in a known manner to be useful for removing the amino-protecting groups (B), with the proviso that when R is —$(CH_2)_3NHCOCH_3$, the amino-protecting group (B) must be tertiobutyloxycarbonyl.

Examples of compounds of Formula II are:
A. Wherein Z is —$CH_2CH_2$— and B is tertiobutyloxycarbonyl:
 xiii R is H:

N¹, N⁴-tertiobutyloxycarbonyl-N¹-2,3-butadienyl-1,4-butanediamine xiv R is methyl, ehtyl, or propyl:
N¹,N⁴-tertiobutyloxycarbonyl-N¹-2,3-butadienyl-N⁴-methyl-1,4-butanediamine
N¹,N⁴-tertiobutyloxycarbonyl-N¹-2,3-butadienyl-N⁴-ethyl-1,4-butanediamine
N¹,N⁴-tertiobutyloxycarbonyl-N¹-2,3-butadienyl-N⁴-propyl-1,4-butanediamine xv R is —CH₂C═C═CH₂:
N¹,N⁴-tertiobutyloxycarbonyl-N¹,N⁴-2,3-butadienyl-1,4-butanediamine xvi R is —CH₂—CH═CH₂:
N¹,N⁴-tertiobutyloxycarbonyl-N¹-2,3-butadienyl-N⁴—1-propenyl-1,4-butanediamine xvii R is —(CH₂)₃NH₂:
N¹,N⁴-tertiobutyloxycarbonyl-N¹-2,3-butadienyl-N⁴-aminopropyl-1,4-butanediamine xviii R is —(CH₂)₃NHCOCH₃:
N¹,N⁴-tertiobutyloxycarbonyl-N¹-2,3-butadienyl-N⁴-acetylaminopropyl-1,4-butanediamine B. Wherein Z is trans-CH═CH₂—:

xix R is H:
(E)-N¹,N⁴-tertiobutyloxycarbonyl-N¹-2,3-butadienyl-2-butene-1,4-diamine xx R is CH₃—, CH₃CH₂—, or CH₃CH₂CH₂—:
(E)-N¹,N⁴-tertiobutyloxycarbonyl-N¹-2,3-butadienyl-N⁴-methyl-2-butene-1,4-diamine
(E)-N¹,N⁴-tertiobutyloxycarbonyl-N¹-2,3-butadienyl-N⁴-ethyl-2-butene-1,4-diamine
(E)-N¹,N⁴-tertiobutyloxycarbonyl-N¹-2,3-butadienyl-N⁴-propyl-2-butene-1,4-diamine xxi R is —CH₂CH═C═CH₂:
(E)-N¹,N⁴-tertiobutyloxycarbonyl-N¹,N⁴-2,3-butadienyl-2-butene-1,4-diamine xxii R is —CH₂CH═CH₂:
(E)-N¹,N⁴-tertiobutyloxycarbonyl-N¹-2,3-butadienyl-N⁴-1-propenyl-2-butene-1,4-diamine xxiii R is —(CH₂)₃NH₂:
(E)-N¹,N⁴-tertiobutyloxycarbonyl-N¹-2,3-butadienyl-N⁴-aminopropyl-2-butene-1,4-diamine xxiv R is —(CH₂)₃NHCOCH₃:
(E)-N¹,N⁴-tertiobutyloxycarbonyl-N¹-2,3-butadienyl-N⁴-acetylaminopropyl-2-butene-1,4-diamine.

The amino-protecting groups (B) are chosen with regard to the nature of the relevant reactions used to prepare the particular compounds of Formula II and having regard to the ease of their removal. The protecting groups include lower alkanoyl, e.g. acetyl, propionyl and trifluoroacetyl; aroyl, e.g. benzoyl, toluoyl; lower alkoxycarbonyl, for example, methoxycarbonyl, ethoxycarbonyl and tertiobutoxycarbonyl; carbobenzoxy; benzenesulfonyl; and tosyl.

In the preparation of the compounds of Formula II, the protecting groups are introduced in a known manner such as the reaction of an appropriate primary or secondary amine with a lower alkanoyl or aroyl chloride, anhydride, sulfonyl-chloride, tertiobutoxycarbonyloxyimino-2-phenyl-acetonitrile (BOC-ON), or di-tertiobutyl dicarbonate [(BOC)₂O]. A preferred amino-protecting group is tertiobutoxycarbonyl (BOC).

Removal of the protecting groups from the compounds of Formula II is conducted in a manner known to those skilled in the art for the relevant protecting group. Usually, said removal involves hydrolytic cleavage using an organic or mineral acid such as trifluoroacetic acid, hydrochloric acid and the like; or by hydrogen chloride gas under anhydrous conditions. Solvents used will be chosen dependent upon the conditions of protecting group removal. For example, ethers such as diethylether can be used for hydrolytic cleavage with hydrogen chloride gas. If other acid sensitive functional groups are present in the molecule, the acid conditions chosen for the removal of the protecting group must be mild in order to avoid unwanted side reactions. In the case of a carbobenzoxy protecting group, this group can be removed in a known manner via catalytic hydrogenolysis.

The compounds of Formula II wherein Z is —CH₂CH₂— or (trans)—CH═CH—, R is hydrogen and B is tertiobutyloxycarbonyl (BOC) are prepared by the method depicted below in Scheme I starting with a N-tertiobutyloxycarbonyl-γ-aminobutyric acid or N-tertiobutyloxycarbonyl-γ-amino-α,β-dihydrobutyric acid as depicted in Formula III:

$$\underset{\text{HNCH}_2\text{ZCO}_2\text{H}}{\overset{\text{BOC}}{|}} \quad \text{Formula III}$$

wherein Z is —CH₂CH₂— or (trans)—CH═CH—.

SCHEME I $$\text{III} + \text{HC}\equiv\text{CCH}_2\text{NH}_2 \xrightarrow{A} \underset{\text{IV}}{\text{HC}\equiv\text{CCH}_2\text{NH}\overset{O}{\overset{\|}{C}}\text{ZCH}_2\underset{\text{V}}{\overset{\text{BOC}}{\overset{|}{\text{NH}}}}} \xrightarrow{B}$$

$$\underset{\text{VI}}{\text{H}_2\text{C}=\text{C}=\text{CHCH}_2\text{NHCOZCH}_2\overset{\text{BOC}}{\overset{|}{\text{NH}}}} \xrightarrow{C}$$

$$\underset{\text{VII}}{\text{H}_2\text{C}=\text{C}=\text{CHCH}_2\text{NHCH}_2\overset{\cdot}{\text{Z}}\text{CH}_2\overset{\text{BOC}}{\overset{|}{\text{NH}}}} \xrightarrow{D}$$

$$\underset{\text{VIII}}{\text{H}_2\text{C}=\text{C}=\text{CHCH}_2\overset{\text{BOC}}{\overset{|}{\text{N}}}\text{CH}_2\text{ZCH}_2\overset{\text{BOC}}{\overset{|}{\text{NH}}}}$$

In step A of Scheme I, a compound of Formula III is reacted in a known manner with propargylamine (IV) to yield a compound of Formula V. The reaction is conveniently performed in the presence of N,N¹-dicyclohexylcarbodiimide in an organic solvent, for example acetonitrile. The ethynyl group of Compound V can be converted to the allenyl group of Compound VI in a known manner using the general method described by P. Crabbé et al., J.C.S. Chem. Comm. 859–860 (1979) and H. Fillion et al., Tet. Letters, 929–930 (1980) for allenic alcohols. In accordance with this procedure the amino protected derivative of a compound of Formula V is treated with formaldehyde and a secondary amine having a hydrogen atom on the α-carbon atom and heated in an organic solvent in the presence of an inorganic salt. Preferably, the heating utilizes reflux conditions. The preferred amine is diisopropylamine and the preferred inorganic salt is a copper salt, particularly cuprous bromide or cupric chloride. Suitable solvents include dioxane, tetrahydrofuran, 1,2-dimethoxyethane, benzene, acetonitrile and/or toluene. The conversion is deemed to proceed via the corresponding amino protected derivative of the secondary amino propynyl compound.

Compound VI is selectively reduced in Step C in a known manner to a compound of Formula VII. The reduction of the carbonyl group is conveniently achieved by means of lithium aluminium hydride in diethyl ether. Compound VII can thus be converted in a known manner to a compound of Formula VIII utilizing conventional procedures for the introduction of a BOC protecting group on a secondary amine. Thus, for example, the secondary amine can be protected by treatment with ditertiobutyl-carbonate in tetrahydrofuran (THF) at the reflux temperature.

The preparation of N,N⁴-tetiobutyloxycarbonyl-N¹-2,3-butadienyl-1,4-butanediamine from 4-tertiobutyloxycarbonylamino-γ-butyric acid according to the general method of Scheme I is specifically described in Example 1.

In general, the compounds of Formula II wherein Z is —CH₂CH₂— or (trans)—CH=CH— and R is —CH₃, —CH₂CH₃, or —CH₂CH₂CH₃, —CH₂CH=C=CH₂, or —CH₂CH=CH₂ are prepared in a known manner by the reaction of an N-protected-2,3-butadienylamine of Formula IX:

$$H_2C=C=CHCH_2NH\overset{|}{B}$$ Formula IX wherein B is an amino-protecting group, with a compound of Formula X:

$$XCH_2ZCH_2N\overset{|}{R'}\overset{|}{B}$$ Formula X wherein Z is —CH₂CH₂— or (trans)—CH=CH—, B is an amino-protecting group, R' is —CH₃, —CH₂CH₃, or —CH₂CH₂CH₃, —CH₂CH=C=CH₂, or —CH₂CH=CH₂, and X is a leaving group. Preferred leaving groups are: mesylate, tosylate, bromide, or iodide. Iodide is the most preferred leaving group. The reaction can conveniently be carried out in an organic solvent, such as tetrahydrofuran (THF), diethyl ether, dimethylformamide (DMF), or benzene, in the presence of one equivalent of strong base, such as, potassium or sodium hydride, potassium or sodium tertbutoxide, or lithium diisopropylamide, for a period ranging from 10 minutes to 24 hours at −30° C. to 100° C., optimally in the presence of a catalytic amount of sodium iodide. The preferred reaction conditions utilize sodium hydride in DMF at 0° to 25° C. The preparation of N¹,N⁴-tertiobutyl-oxycarbonyl-N¹-2,3-butadienyl-N⁴-methyl-1,4-butanediamine from N-tertiobutyloxycarbonyl-2,3-butadienylamine (IX) and N-tertiobutyloxycarbonyl-N-methyl-4-iodo-1-butenamine (X) is specifically described in Example 4a.

The compounds of Formula II wherein Z is —CH₂CH₂— or (trans)-CH=CH— and R is —CH₂CH=C=CH₂, can also be prepared by the reaction of two equivalents of a compound of Formula IX with a compound of Formula XI:

XCH₂ZCH₂X                 Formula XI wherein Z is —CH₂CH₂— or (trans)-CH=CH— and X is a leaving group, such as those defined with respect to Formula X. This reaction can be conducted in a known manner as previously described with respect to the reaction of a compound of Formula IX with a compound of Formula X. The preparation of N¹,N⁴-tertiobutyloxycarbonyl-N¹,N⁴-2,3-butadienyl-1,4-butanediamine via N-tertiobutyloxycarbonyl-2,3-butadienylamine (IX) and 1,4-diiodobutane (XI) is specifically described in Example 5a. The preparation of (E)-N¹,N⁴-tertiobutyloxycarbonyl-N¹,N⁴-2,3-butadienyl-2-butene-1,4-diamine from N-tertiobutyloxycarbonyl-2,3-butadienylamine and (E)-1,4-dibromo-2-butene is described in Example 6A.

The compounds of Formula II wherein Z is —CH₂CH₂— or (trans)—CH=CH— and R is —(CH₂)₃NHCOCH₃ or —(CH₂)₃NH₂ are made in manner known per se by the reaction sequence depicted below in Scheme II starting from a compound of Formula VIII (see Scheme I):

SCHEME II

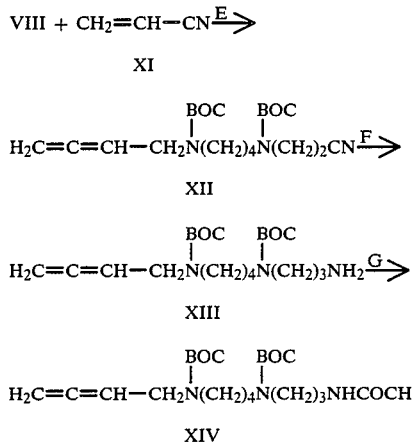

In Step E, a compound of Formula VIII is reacted with acrylonitrile (XI) in a known manner to provide the compound of Formula XII. The reaction is performed in the presence of a base in an organic solvent.

In Step F, compound XII is reduced to yield the compound of Formula XIII in a known manner utilizing conventional (non-catalytic) methods for the selective reduction of a cyano group to a primary amino group. The preferred reagent is lithium aluminium hydride. The preparation of the N-acetyl derivative of Formula XIV from Compound XIII is carried out in a manner known to those skilled in the art using conventional acetylation techniques.

The N-protected 2,3-butadienyl amine compounds of Formula IX can be prepared in a known manner from an N-protected proparagyl amine of Formula XV:

HC≡CCH₂NHB             Formula XV wherein B is an amino-protecting group as previously defined. The procedure for carrying out this transformation is described above with respect to Step B in Scheme 1. The specific preparation of N-tertiobutyloxycarbonyl-2,3-butadienylamine from N-tertiobutyloxypropargylamine is described in Example 3.

The compounds of Formula X can be prepared in a known manner utilizing an N-protected-γ-aminobutyric acid or N-protected-γ-amino-α,β-dihydro-butyric acid of Formula IIIa:

Formula IIIa wherein B is an amino-protecting group and Z is —CH₂CH₂ or (trans)—CH═CH—, using the method depicted below in Scheme III or Scheme IV.

Scheme III is preferred for the preparation of compounds of Formula X wherein R is —CH₃, —CH₂CH₃, or —CH₂CH₂CH₃ (the compounds of general Formula XVIII, below).

SCHEME III

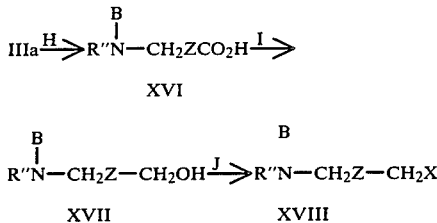

In Scheme III, the symbol B is an amino-protecting group, R" is —CH₃, —CH₂CH₃, or —CH₂CH₂CH₃, and X is a leaving group. In Step H, a compound of Formula IIIa is alkylated in a known manner to yield a compound of Formula XVI. The alkylation can be conducted by the reaction of a compound of Formula IIIa with 2 equivalents of a strong base, such as sodium hydride, in an aprotic solvent, such as THF, and then treating the anion thus formed with a suitable alkylating agent (RX) wherein X is a leaving group, preferably iodide.

Compound XVI is reduced to the corresponding alcohol of Formula XVII in Step I in known procedures utilizing a reagent capable of reducing the carboxylic acid function without affecting the N-protecting group. A suitable reagent for this reduction is diborane.

In Step J, an alcohol of Formula XVII is converted to a compound of Formula XVIII using conventional methods suitable for the replacement of an -OH group by a leaving group. The preparation of N-tertiobutyloxycarbonyl-N-methyl-4-iodo-1-butanamine (X) from 4-tertiobutyloxycarbonylamine-1-butyric acid (IIIa) is further described in Examples 2a, 2b, 2c, and 2d.

Scheme IV is preferred for the preparation of compounds of Formula X wherein R is —CH₂CH═C═CH₂ or —CH₂CH═CH₂ (the compounds of Formula XXI).

SCHEME IV

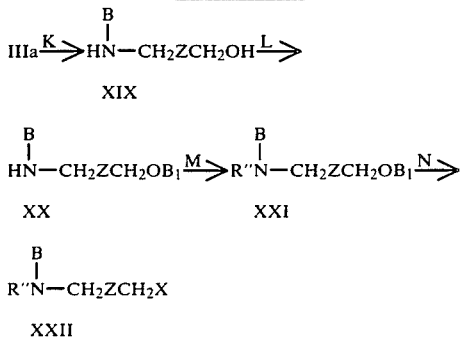

In Scheme IV, R" is —CH₂CH═CH₂ or —CH₂CH═C═CH₂, B₁ is a protecting group for an OH group. In Step K, a compound of Formula IIIa is selectively reduced in a known manner to yield the alcohol of Formula XIX. A suitable method for the reaction is described in Step I of Scheme III.

The OH group of compound XIX is thus protected in Step L via known procedures to yield a compound of Formula XX. Suitable protecting groups for the OH group are those that can be removed under mild acidic conditions, for example tetrahydropyranyl or methoxymethyl.

Compound XX is alkylated in Step M via known procedures to yield a compound of Formula XXI. A suitable procedure is described in Step H of Scheme III above, with the proviso that only one equivalent of base is employed.

In the final reaction, Step N, compound XXI is converted to a compound of Formula XXII via known methods useful in the replacement of an —OH group by a leaving group (X).

The following Examples further illustrate the invention and are not intended to limit the invention in any way:

EXAMPLE 1

N-2,3-Butadienyl-1,4-butanediamine

A. 4-Tertiobutyloxycarbonylamino-N-(2-propynyl) butanamide

To a solution of 4-tertiobutyloxycarbonyl aminobutyric acid (5.05 g, 25 mM) and propargylamine (1.71 ml, 25 mM) in acetonitrile (120 ml) cooled to 0° C. was added under nitrogen a solution of N,N¹-dicyclohexylcarbodiimide (5.15 g, 25 mM) in acetonitrile (20 ml). The temperature of the reaction mixture was slowly raised to 20° C., and stirring was continued for 12 h. Concentration in vacuo left a solid residue which was chromatographed on silica gel (400 g). Elution with a gradient of ethyl acetate/dichloromethane (1/5 to 2/5) gave the title compound after recrystallization from ethylacetate; mp 147° C.

B. 4-Tertiobutyloxycarbonylamino-N-(2,3-butadienyl) butanamide

A mixture of 4-tertiobutyloxycarbonylamino-N-(2-propynyl) butanamide (2.4 g, 10 mM), prepared as in Part A, diisopropylamine (1.68 ml, 12 mM), cuprous bromide (0.474 g, 3.3 mM), formaldehyde (1.19 ml of a 37% solution in water, 16 mM) in dioxane (20 ml) was treated at reflux temperature for 1 h. The reaction mixture was then quenched with water and extracted with methylene chloride (3×40 ml). The organic layers were pooled and washed with 1 N acetic acid, water, and brine, and dried over magnesium sulfate (MgSO₄). Concentration in vacuo left a solid residue (2.4 g) which was chromatographed on silica gel (150 g). Elution with ethyl acetate/chloroform 1/5) yielded the title compound after recrystallization in dichloromethane/pentane; mp 92° C.

C.

N¹,N⁴-Tertiobutyloxycarbonyl-N¹-2,3-butadienyl-1,4-butanediamine

To a suspension of lithium aluminium hydride (1.19 g, 31 mM) in anhydrous diethyl ether (150 ml) cooled to 0° C. was added a solution of 4-tertiobutyloxycarbonylamino-N-(2,3-butadienyl)butanamide, prepared as in Part B (1.59 g, 6.3 mM) in anhydrous tetrahydrofuran (THF, 6 ml). After stirring for 54 h at room temperature, the reaction mixture was quenched successively with water (1.19 ml), 15% aqueous sodium hydroxide (1.19 ml), and water (3.57 ml). The aluminium salts were filtered and washed extensively with diethyl ether. The filtrate was concentrated in vacuo to afford $N^4$-tertiobutyloxycarbonyl-$N^1$-2,3-butadienyl-1,4-butanediamine contaminated with a small amount of $N^1$-2,3-butadienyl-$N^4$-methyl-1,4-butanediamine as an oily residue (995 mg). This residue was dissolved in THF (40 ml). Ditertio-butyloxycarbonate (0.9 g, 4.15 mM) was added, and the mixture was heated at reflux temperature for 4 h. Diethyl ether (100 ml) was added, and the organic phase was washed with water (3×20 ml), dried over MgSO₄, and concentrated in vacuo. The residue was purified by flash chromatography on silica gel (100 g). Elution with diethyl ether/petroleum ether (1/9) afforded $N^1,N^4$-tertiobutyloxycarbonyl-$N^1$-2,3-butadienyl-$N^4$-methyl-1,4-butanediamine (165 mg), then a mixture of $N^1,N^4$-tertiobutyloxycarbonyl-$N^1$-(2,3-butadienyl)-1,4-butanediamine and the former compound (344 mg), and finally pure $N^1,N^4$-tertiobutyloxycarbonyl-$N^1$-(2,3-butadienyl)-1,4-butanediamine (365 mg) as an oil:

IR (CH₂Cl₂): 1950 cm⁻¹(allene), 1680 cm⁻¹, 1700 cm⁻¹(—CO—);

NMR (CDCl₃): 5 ppm 1.46 (C(CH₃)₃, 18 H, s), 2.9–3.4 (CH₂—N, 4 H, m), 3.6–4.0 (=-CH₂—N, 2 H, m),

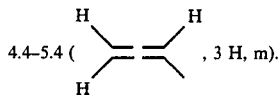

D. N-2,3-Butadienyl-1,4-butanediamine

To a solution of $N^1,N^4$-tertiobutyloxycarbonyl-$N^1$-2,3-butadienyl-1,4-butanediamine, prepared as in Part C (0.3 g), in absolute ethanol (4 ml) was added a solution of anhydrous HCl (3.7 M) in diethyl ether (4 ml). The mixture was left standing 4 h at room temperature and 20 h at 0° C. The crystals which formed slowly were filtered and recrystallized from absolute ethanol to give the title compound, as the dihydrochloride (170 mg): mp 197° C.;

NMR (D₂O) δ ppm: 1.8–2.0 (—CH₂—, 4 H, m), 2.8–3.4 (CH₂—N, 4 H, m), 3.5–3.8 (=CH₂—N, 2 H, m),

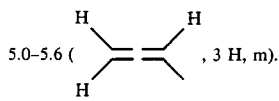

EXAMPLE 2

N-Tertiobutyloxycarbonyl-N-methyl-4-iodobutanamine

A. 4-Tertiobutyloxycarbonylamino-1-butyric acid

A mixture of GABA (51.5 g) and ditertiobutyl carbonate (109.12 g) in THF (100 ml) and water (100 ml) was heated under reflux temperature for 2 h. The solvents were concentrated in vacuo and the residue extracted with ether. The organic layers were pooled, washed with brine, and dried over MgSO₄. Concentration in vacuo gave the title compound (87.8 g); mp 51° C., recrystallized from pentane/Et₂O at −80° C.;

NMR (CDCl₃) δ: 1.45 (C(CH₃)₃, 9 H, s).

B. N-Tertiobutyloxycarbonyl-N-methyl-4-amino-1-butyric acid

To a suspension of sodium hydride (9.6 g of a 55% suspension in oil washed 3 times in pentane) in anhydrous THF (250 ml) was added a solution of 4-tertiobutyloxycarbonylamino-1-butyric acid, prepared as in Part A (20.3 g), in anhydrous THF (250 ml). The mixture was stirred for 20 h at 25° C. and then methyl iodide (13.64 ml) was added. After 3 h at 25° C., the reaction mixture was quenched with brine, neutralized with acetic acid and extracted with diethyl ether many times. The organic layers were pooled, washed with brine, and dried over MgSO₄. Concentration in vacuo left an oily residue which was crystallized from diethyl ether/pentane to afford the title compound (17 g); mp 61° C.;

NMR (CDCl₃): 1.43 (C(CH₃)₃, s, 9 H), 2.83 (N—CH₃, s, 3 H).

C. N-Tertiobutyloxycarbonyl-N-methyl-4-hydroxy-1-butanamine

To a solution of N-tertiobutyloxycarbonyl-N-methyl-4-amino-1-butyric acid, prepared as in Part C (10.08 g) in anhydrous THF (100 ml) cooled to −78° C. was added under nitrogen a solution of borane (1 M) in THF (75 ml). The temperature was allowed to rise to 25° C. and stirring was continued for 20 h at 25° C. whereupon the excess of borane was destroyed by addition of methanol. Concentrated acetic acid was then added until the pH of the solution became acidic. The solvent was concentrated in vacuo and the residue extracted with diethyl ether. The organic layer was washed with water, an aqueous solution of bicarbonate, and then brine, dried over MgSO₄, and then concentrated in vacuo to yield the title compound (9.08 g) as an oil, which was used in the next step without further purification.

NMR (CDCl₃): 1.46 (C(CH₃)₃, s), 2.83 (N—CH₃, s, 3 H).

D. N-Tertiobutyloxycarbonyl-N-methyl-4-iodo-1-butanamine

To a solution of N-tertiobutyloxycarbonyl-N-methyl-4-hydroxy-1-butanamine, prepared as in Part C (4.84 g), and triethylamine (5 ml) in methylene chloride (75 ml) cooled to −10° C. was added dropwise a solution of mesylchloride (3 g) in methylene chloride (25 ml). Stirring was continued for 15 min at −10° C. The reaction mixture was then quenched with water. The organic layer was washed consecutively with aqueous acetic acid (1 N), aqueous sodium bicarbonate, water, and brine, dried over MgSO₄, and concentrated in vacuo to afford the corresponding mesylate (6.29 g, 0.22 mol) as an oil.

NMR (CDCl₃): 1.46 (C(CH₃)₃, s), 2.83 (N—CH₃, s, 3 H), 3.0 (CH₃OSO₂, s, 3 H).

The mesylate (6.29 g) was dissolved in anhydrous diethyl ether (75 ml). The solution was cooled to −10° C. Then a solution of 0.15 M magnesium iodide (150 ml) in anhydrous ether was added under vigorous stirring. The reaction mixture was quenched with water. The etheral layer was washed with water, aqueous bisulfite and brine, dried over MgSO$_4$, and concentrated in vacuo to yield the title compound (6.25 g) as an oil.

NMR (CDCl$_3$): 1.46 (C(CH$_3$)$_3$, s), 2.8 (N—CH$_3$, 3 H, s).

EXAMPLE 3

N-Tertiobutyloxycarbonyl-2,3-butadienylamine

A mixture of N-tertiobutyloxycarbonyl propargylamine (14.77 g, 0.0953 mol), diisopropylamine (19.97 ml, 0.114 mol), formaldehyde (19.58 ml of a 37% aqueous solution, 0.213 mol), and CuBr (4.1 g, 0.029 mol) in dioxane (180 ml) was heated at reflux temperature for 12 h under nitrogen. Upon cooling the solution was diluted with diethyl ether (~500 ml). Then acetic acid was added until the pH of the solution reached the value of 4. The organic layer was washed many times with water and then brine, dried over MgSO$_4$, and concentrated in vacuo to yield a brown oil (13 g) which was purified by flash chromatography (300 g of silica gel; elulant: diethyl ether/petroleum ether 1/9) to afford the title compound (10.14 g) as an oil.

TLC: Rf=0.66 (Et$_2$O/Pet. ether ¼);

NMR (CDCl$_3$): 1.45 (C(CH$_3$)$_3$, 9 H, s), 3.46–3.94 (—CH$_2$—N, 2 H, m), 4.5–5.4 ( 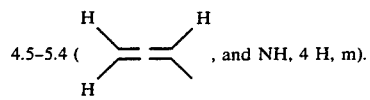 , and NH, 4 H, m).

EXAMPLE 4

N$^1$-2,3-Butadienyl-N$^4$-methyl-1,4-butanediamine

A.

N$^1$,N$^4$-Tertiobutyloxycarbonyl-N$^1$-2,3-butadienyl-N$^4$-methyl-1,4-butanediamine To a suspension of sodium hydride (0.87 g of a 55% suspension in oil washed 3 times with pentane, 0.02 mmol) in anhydrous dimethylformamide (30 ml) cooled to 0° C. was added under nitrogen a solution of N-tertiobutyloxycarbonyl-N-methyl-4-iodobutanamine, prepared as in Example 2 (6.25 g, 0.02 mol), in anhydrous dimethylformamide (20 ml). Then a solution of N-tertiobutyloxycarbonyl-2,3-butadienylamine prepared as in Example 3 (3.38 g, 0.02 mol) in anhydrous dimethylformamide (30 ml) was added over a period of 20 min. Stirring was continued for 2½ h at 0° C. Then the reaction mixture was quenched with water and extracted with diethyl ether (5×100 ml). The organic layers were pooled, washed with water and then brine, and dried over MgSO$_4$. Concentration in vacuo gave an oil residue (8.3 g) which was purified by flash chromatography (400 g silica gel; eluant: diethyl ether/petroleum ether, ¼) to afford the title compound (5.5 g) as an oil.

TLC: Rf=0.3 (diethyl ether/petroleum ether—25/75);

NMR (CDCl$_3$): δ1.45 (C(CH$_3$)$_3$ and —CH$_2$CH$_2$—, 22 H), 2.83 (N—CH$_3$, 3 H, s), 4.6–5.4 ( 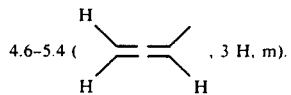 , 3 H, m).

IR (CH$_2$Cl$_2$): 1950 cm$^{-1}$ ( 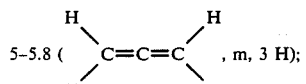 ), 1675 cm$^{-1}$ (HNCO$_2$—);

MS (CI, CH$_4$): m/e 355.

Analysis for C$_{19}$H$_{34}$N$_2$O$_4$: Calc. C, 64.38; H, 9.68; N, 7.90% Found C, 63.92; H, 9.48; N, 7.39%

The analytical sample was prepared by distillation with a "cold finger" apparatus (temperature oil bath 130° C., 0.3 mm Hg).

B. N$^1$-2,3-Butadienyl-N$^4$-methyl-1,4-butanediamine

To a solution of N$^1$,N$^4$-tertiobutyloxycarbonyl-N$^1$-2,3-butadienyl-N$^4$-methyl-1,4-butanediamine, prepared as in Part A (4.9 g), in absolute ethanol (25 ml) was added a solution of anhydrous HCl (2 M) in diethyl ether (80 ml). The mixture was left standing for 4 h at 25° C. and then for 20 h at 4° C. The crystals which formed slowly were filtered and washed with anhydrous diethyl ether to yield the title compound as the dihydrochloride, analytically pure (2.86 g); mp 226° C.

NMR (D$_2$O: δ280 (N—CH$_3$, 3 H, s),

5–5.8 ( 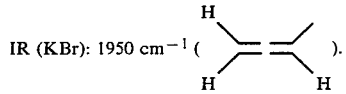 , m, 3 H);

IR (KBr): 1950 cm$^{-1}$ ( 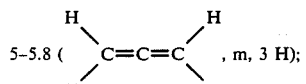 ).

EXAMPLE 5

N$^1$N$^4$-2,3-Butadienyl-1,4-butanediamine

A.

N$^1$,N$^4$-Tertiobutyloxycarbonyl-N$^1$,N$^4$-2,3-butadienyl-1,4-butanediamine

To a suspension of sodium hydride (2.4 g of a 55% oil suspension washed 3 times with pentane, 0.055 mol) in anhydrous dimethylformamide (50 ml) cooled to 0° C., was added under nitrogen, a solution of 1,4-diiodobutane (7.75 g, 0.025 mol) in anhydrous dimethylformamide (10 ml). Then a solution of N-tertiobutyloxycarbonyl-2,3-butadienylamine, prepared as in Example 3 (8.45 g, 0.05 mol) in anhydrous dimethylformamide (40 ml) was added over a period of 25 min. Stirring was continued for 3 h at 25° C. The reaction mixture was then quenched with water and extracted with ether (5×150 ml). The organic layers were pooled, washed with water, and then brine, and dried over MgSO$_4$. Concentration in vacuo gave an oily residue (8.88 g) which was purified by flash chromatography (300 g silica gel; eluant: gradient of diethyl ether/petroleum ether from 5/95 to 20/80) to afford a complex mixture of unidentified compounds (4.4 g) and the title compound (4.11 g) as an oil.

TLC: Rf=0.3 (eluant:diethyl ether/petroleum ether 25:75);

NMR (CDCl$_3$): δ 4.6–5.3 ( 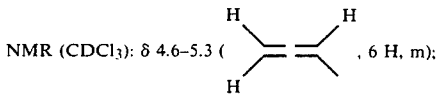 , 6 H, m);

1.45 (C(CH$_3$)$_3$, —CH$_2$—, 22 H, s);
IR (CH$_2$Cl$_2$): 1950 cm$^{-1}$(=.=), 1675 cm$^{-1}$(—N-CO$_2$—);
MS (CI, CH$_4$) m/e MH$^+$393.
Analysis for C$_{22}$H$_{36}$N$_2$O$_4$:
Calc. C, 67.32; H, 9.24; N, 7.14%
Found C, 67.76; H, 9.12; N, 6.63%.
The analytical sample was prepared by distillation with a "cold finger" apparatus (temp. oil bath 95° C., 0.01 mm Hg).

B. N$^1$,N$^4$-2,3-Butadienyl-1,4-butanediamine

To a solution of N$^1$,N$^4$-tertiobutyloxycarbonyl-N$^1$,N$^4$-2,3-butadienyl-1,4-butanediamine, prepared as in Part A (4.1 g), in absolute ethanol (25 ml) was added a solution of anhydrous HCl (2 M) in anhydrous diethylether (80 ml). The mixture was left standing for 4 h at 25° C. and then for 20 h at 4° C. The crystals which formed slowly were filtered and washed with diethyl ether to yield the title compound as the dihydrochloride, analytically pure (2.63 g); mp 242° C.
NMR (D$_2$O): δ1.5–2.0 (—CH$_2$—, 4 H, m), 2.8–3.3 (—CH$_2$—N, 4 H, m), 3.4–3.9 (=—CH$_2$—N, 4H, m),

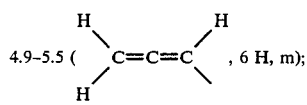
4.9–5.5 ( , 6 H, m);

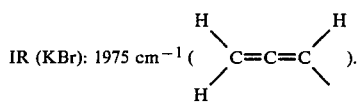
IR (KBr): 1975 cm$^{-1}$ ( ).

EXAMPLE 6

(E)-N$^1$,N$^4$-2,3-Butadienyl-2-butene-1,4-diamine

A.
(E)-N$^1$,N$^4$-Tertiobutyloxycarbonyl-N$^1$,N$^4$-2,3-butadienyl-2-butene-1,4-diamine To a suspension of sodium hydride (0.426 g of a 55% suspension in oil washed 3 times with pentane, 9.82 mmol) and sodium iodide (catalytic amount) in anhydrous dimethylformamide (DMF, 9 ml) cooled to 0° C. was added under nitrogen a solution of (E)-1,4-dibromo-2-butene (1.05 g, 4.91 mmol) in anhydrous DMF (4 ml). Then a solution of N-tertiobutyloxycarbonyl-2,3-butadienyl amine, prepared as in Example 3 (1.66 g) in anhydrous DMF was added dropwise over a period of 20 min. Stirring was continued for 30 min at 0° C. The reaction mixture was then quenched with water and extracted with diethylether (4×50 ml). The organic layers were pooled, washed with water, and then brine, and dried over MgSO$_4$. Concentration in vacuo afforded an oil (2.02 g) which was purified by flash chromatography (200 g of silica gel; eluant gradient of diethyl ether in petroleum ether 10 to 25%) to give the starting allenyl amine derivative (0.4 g) and the title compound (1.09 g) as an oil. The analytical sample was prepared by distillation with a "cold finger" apparatus (temp. oil bath: 125° C., 0.4 mm Hg).
NMR (CDCl$_3$): δ1.45 (C(CH$_3$)$_3$, 18 H, s), 3.57–4.0 (CH$_2$-N, 8 H, m),

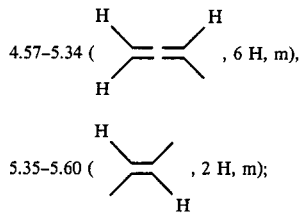
4.57–5.34 ( , 6 H, m), 5.35–5.60 ( , 2 H, m);

IR (CH$_2$Cl$_2$): 1950 cm$^{-1}$(=.=) 1680 cm$^{-1}$(—N-CO$_2$—);
MS (CI, NH$_3$) m/e MH$^+$: 391.

B. (E)-N$^1$,N$^4$-2,3-Butadienyl-2-butene-1,4-diamine

To a solution of (E)-N$^1$,N$^4$-tertiobutyloxycarbonyl-N$^1$,N$^4$-2,3-butadienyl-2-butene-1,4-diamine, prepared as in Part A (0.994 g), in absolute ethanol (4 ml) was added a solution of anhydrous HCl (2 M) in anhydrous diethyl ether (12 ml). The mixture was left standing for 6 h at 25° C. and then for 20 h at 4° C. The crystals which formed slowly were filtered and washed with anhydrous diethyl ether to yield the title compound analytically pure (0.555 g); mp 222° C.
NMR (D$_2$O): 3.4–4.0 (—CH$_2$N, 4 H, m),

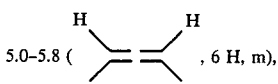
5.0–5.8 ( , 6 H, m),

6.0–6.3 ( , 2 H, m);

IR (KBr): 1950 cm$^{-1}$ (allene).

EXAMPLE 7

The ability of the compounds of Formula I to inhibit PAO in vitro can be demonstrated according to the following test procedure:

Measurement of kinetic constants:

Method:

Partially purified PAO from pig liver (forming 2.2 nmol N$^1$-acetylspermidine/mg protein/h from N$^1$,N$^{12}$-diacetylspermine) was preincubated with the inhibitor at 30° C. in borate buffer at pH 9.0. The remaining enzyme activity was determined by measurement of the hydrogen peroxide formed [H. Snyder et al., J. Pharm. Exptl. Therap., 63, 386 (1968)] during the oxidation of N$^1$,N$^{12}$-diacetylspermine.

Results:

| Example | R$_1$ | R$_2$ | R$_3$ | R$_4$ | K$_I$(μM) | τ½ (min) |
|---|---|---|---|---|---|---|
| 1 | ⫽⟋ | H | H | H | 0.7 | 1 |
| 4 | ⫽⟋ | H | H | CH$_3$ | 0.34 | 0.5 |

-continued

[Structure: R₂(R₁)N-CH₂CH₂CH₂CH₂-N(R₃)(R₄)]

| Example | $R_1$ | $R_2$ | $R_3$ | $R_4$ | $K_I$ (μM) | $\tau_{\frac{1}{2}}$ (min) |
|---------|-------|-------|-------|-------|------------|------|
| 5 | CH₂CH=C=CH₂ | H | H | CH₂CH=C=CH₂ | 0.09 | 2.2 |

EXAMPLE 8

The ability of the compounds of Formula II to inhibit PAO ex vivo can be demonstrated according to the following test procedure:

Measurement of PAO activities in mouse tissues:

Method:

PAO Activity was measured ex vivo in mouse tissue homogenates using $N^1,N^{12}$-diacetylspermine as substrate. $N^1$-Acetylspermidine was determined using a dansylation method [N. Seiler et al., Biochim. Biophys. Acta, 615, 480 (1980)].

Results:

$N^1$-2,3-Butadienyl-$N^4$-methyl-1,4-butanediamine, dihydrochloride (Example 4):

The dose-response in mice for PAO-inhibition was obtained at 4 h after i.p. injection. $ID_{50}$-values for liver, epididymis, spleen and kidney are between 0.05 and 0.1 mg/kg i.p.. Complete inhibition in these organs can be achieved with a dose of 1 mg/kg i.p.. The inhibition is irreversible; PAO is not reactivated in vitro by incubation with its substrate. For mouse brain-PAO the $ID_{50}$ is 5 mg/kg i.p.: inhibition is complete at 10 mg/kg.

$N^1,N^4$-2,3-Butadienyl-1,4-butanediamine, dihydrochloride (Example 5):

At a dose of 20 mg/kg i.p., this compound is equipotent to $N^1$-2,3-butadienyl-$N^4$-methyl-1,4-butanediamine, dihydrochloride (Example 4) in inhibiting PAO in vivo.

I claim:

1. A compound of the formula:

$$H_2C=C=CHCH_2NHCH_2-Z-CH_2NHR$$

wherein:

Z is —CH₂CH₂— or trans—CH=CH—,

R is H, CH₃—, CH₃CH₂, CH₃(CH₂)₂—, —(CH₂)₃NH₂, —(CH₂)₃NHCOCH₃, —CH₂CH=CH₂, or —CH₂CH=C=CH₂, or a pharmaceutically acceptable acid addition salt thereof.

2. The compound as defined in claim 1 which is N-2,3-butadienyl-1,4-butanediamine.

3. The compound as defined in claim 1 which is $N^1$-2,3-butadienyl-$N^4$-methyl-1,4-butanediamine.

4. The compound as defined in claim 1 which is $N^1$-2,3-butadienyl-$N^4$-ethyl-1,4-butanedeamine.

5. The compound as defined in claim 1 which is $N^1$-2,3-butadienyl-$N^4$-propyl-1,4-butanediamine.

6. The compound s defined in claim 1 which is $N^1,N^4$-2,3-butadienyl-1,4-butanediamine.

7. The compound as defined in claim 1 which is $N^1$-2,3-butadienyl-$N^4$-1-propenyl-1.4-butanediamine.

8. The compound as defined in claim 1 which is $N^1$-2,3-butadienyl-$N^4$-aminopropyl-1,4-butanediamine.

9. The compound as defined in claim 1 which is $N^1$-2,3-butadienyl-$N^4$-acetylaminopropyl-1,4-butanediamine.

10. The compound as defined in claim 1 which is (E)-N-2,3-butadienyl-2-butene-1,4-diamine.

11. The compound as defined in claim 1 which is (E)-N-2,3-butadienyl-$N^4$-methyl-2-butene-1,4-diamine.

12. The compound as defined in claim 1 which is (E)-N-2,3-butadienyl-$N^4$-ethyl-2-butene-1,4-diamine.

13. The compound as defined in claim 1 which is (E)-N-2,3-butadienyl-$N^4$-propyl-2-butene-1,4-diamine.

14. The compound as defined in claim 1 which is (E)-$N^1,N^4$-2,3-butadienyl-2-butene-1,4-diamine.

15. The compound as defined in claim 1 which is (E)-$N^1$-2,3-butadienyl-$N^4$-1-propenyl-2-butene-1,4-diamine.

16. The compound as defined in claim 1 which is (E)-$N^1$-2,3-butadienyl-$N^4$-aminopropyl-2-butene-1,4-diamine.

17. The compound as defined in claim 1 which is (E)-$N^1$-2,3-butadienyl-$N^4$-acetylaminopropyl-2-butene-1,4-diamine.

* * * * *

UNITED STATES PATENT AND TRADEMARK OFFICE
CERTIFICATE OF CORRECTION

PATENT NO. : 4,551,550

DATED : November 5, 1985

INVENTOR(S) : Philippe Bey

It is certified that error appears in the above-identified patent and that said Letters Patent is hereby corrected as shown below:

Column 1, line 4:

Insert as a separate paragraph after the title:

-- This is a continuation-in-part of application Serial Number 669,416, filed November 8, 1984, now abandoned, which is a continuation-in-part of application Serial Number 558,642, filed December 6, 1983, now abandoned. --

Signed and Sealed this

Fifteenth Day of March, 1994

*Attest:*

BRUCE LEHMAN

*Attesting Officer*    *Commissioner of Patents and Trademarks*